United States Patent [19]

Rodwell et al.

[11] Patent Number: 5,047,227
[45] Date of Patent: Sep. 10, 1991

[54] NOVEL AND IMPROVED ANTIBODIES FOR SITE SPECIFIC ATTACHMENT OF COMPOUNDS

[75] Inventors: John D. Rodwell, Yardley; Thomas J. McKearn, New Hope, both of Pa.; Cynthia G. Long, Skillman, N.J.

[73] Assignee: Cytogen Corporation, Princeton, N.J.

[21] Appl. No.: 650,363

[22] Filed: Feb. 4, 1991

Related U.S. Application Data

[63] Continuation of Ser. No. 153,175, Feb. 8, 1988, abandoned.

[51] Int. Cl.$^5$ .................. A61K 49/02; A61K 39/44
[52] U.S. Cl. ............................ 424/1.1; 424/9; 424/85.8; 424/85.91; 530/387; 530/388; 530/390; 530/391; 530/395
[58] Field of Search ............... 424/1.1, 9, 85.91, 85.8; 530/390, 391, 395, 387, 388

[56] References Cited

U.S. PATENT DOCUMENTS

| | | |
|---|---|---|
| 3,447,893 | 10/1974 | Reading ........................ 436/547 |
| 4,217,338 | 8/1980 | Quash ............................ 424/1.1 |
| 4,419,444 | 12/1987 | Quash ............................. 435/7 |
| 4,634,666 | 1/1987 | Engleman et al. .............. 435/68 |
| 4,671,958 | 6/1987 | Rodwell et al. ............. 424/85.91 |
| 4,699,784 | 10/1987 | Shih et al. ................. 424/85.91 |
| 4,925,796 | 5/1990 | Bergh et al. .................... 435/97 |

FOREIGN PATENT DOCUMENTS

| | | |
|---|---|---|
| 173629 | 3/1986 | European Pat. Off. . |
| 175617 | 3/1986 | European Pat. Off. . |

OTHER PUBLICATIONS

O'Shannessy et al., Immunology Letters, 8: 273–177 (1984).
Rodwell et al., Proc. Natl. Acad. Sci. U.S.A., 83: 2632–2636 (1986).
Bunton, in Oxidation in Organic Chemistry, vol. I, Widberg, ed., Academic Press, New York, p. 367 (1965).
Cole et al., in Monoclonal Antibodies and Cancer Therapy, Alan R. Liss, Inc., pp. 77–96 (1985).
Fuhrmann et al., Nature, 307: 755≅758 (1984).
Jackson, "Periodic Acid Oxidations" in Organic Reactions, vol. 2, pp. 341–375 (1944).
Jentoft and Dearborn, J. Biol. Chem., 254: 4359–4365 (1979).
Johnson and Laguzza, Cancer Res., 47: 3118–3122 (1987).
Kohler and Milstein, Sci. Amer., 243: 66–74 (1980).
Kozbor et al., Immunol. Today, 4: 72 (1983).
March, in Advanced Organic Chemistry: Reactions, Mechanisms and Structures, McGraw-Hill Co., New York, pp. 824–825 (1978).
Steer et al (1986), Progress in Liver Disease III, chapt. 6, pp. 99–123.
*Biochemistry*, 3rd ed by L. Stryer, 1988, Freeman and Company, N.Y., pp. 344 and 777.

*Primary Examiner*—John Doll
*Assistant Examiner*—Kay Kim
*Attorney, Agent, or Firm*—Pennie & Edmonds

[57] ABSTRACT

Novel and improved antibody compositions comprising an antibody or antibody fragment having an increased number of sites on a carbohydrate side chain available for the site specific attachment of a compound to a region of the antibody or antibody fragment which is not part of nor directly involved with the antigen binding site are disclosed. Conjugates, prepared using the high-mannose-containing antibodies, which are characterized by substantially the same immunospecificity as the unmodified unconjugated antibody molecule, are also disclosed. The antibody compositions are advantageously used for a wide variety of therapeutic and diagnostic applications in both in vivo and in vitro targeted delivery systems and assays. Methods for preparing the antibody compositions, as well as antibody conjugate intermediates, and methods for using the antibody compositions are also described.

16 Claims, No Drawings

NOVEL AND IMPROVED ANTIBODIES FOR SITE SPECIFIC ATTACHMENT OF COMPOUNDS

This is a continuation, of application Ser. No. 07/153,175 filed Feb. 8, 1988, now abandoned.

FIELD OF THE INVENTION

The present invention relates to the general area of antibody systems for the delivery of compounds to target sites in vivo or in vitro. Such systems include delivery systems for in vivo as well as in vitro therapeutic purposes, in vivo and in vitro diagnostic purposes, e.g., imaging, in vitro assays, cell sorting systems and separation schemes based on an antibody-antigen interaction.

More particularly, the invention is directed to improved compositions comprising antibodies or antibody fragments having an increased number of sites on the carbohydrate side chain available for the site specific attachment of a compound.

BACKGROUND OF THE INVENTION

Carbohydrate side-chains are attached to antibody molecules via the dolichol-dependent, asparagine-linked pathway (Granato et al., 1987, Mol. Immunol 24:849–55). In general, one main species of oligosaccharide chain, composed of glucose, mannose and N-acetylglucosamine residues ($Glc_3Man_9GlcNAc_2$) is transferred to the protein moiety of the antibody in the endoplasmic reticulum (ER). The $Glc_3Man_9GlcNAc_2$ precursor oligosaccharide is attached to an $NH_2$ group on a side chain of an asparagine residue of the protein. The diversity of the carbohydrate side chains results from structural modifications of this single precursor oligosaccharide which begin in the ER and continue during subsequent transit of the nascent glycoprotein through the Golgi apparatus. Indeed, the carbohydrate side chains of the mature antibody molecule result from the activity of a variety of glycosidases that "trim" glucose and mannose residues from the oligosaccharide precursor as well as the activity of other enzymes that add GlcNAc, fucose, galactose and sialic acid residues.

Specific inhibitors which block different enzymes in the trimming process of the biosynthesis of glycoproteins have been known for a number of years (see, e.g., Gross et al., 1983, J. Biol. Chem. 256:12203-09). For instance, 1-deoxynojirimycin has been shown to inhibit glucosidases I and III; swainsonine, to inhibit mannosidase II; and bromoconduritol, to inhibit trimming of the innermost glucose residue of $Glc_3Man_9GlcNAc_2$ (see, Gross et al., supra). Castanospermine has been shown to inhibit some beta-glucosidases (Saul et al., 1983, Arch. Biochem. Biophys. 221:593).

SITE SPECIFIC ATTACHMENT TO A CARBOHYDRATE MOIETY OF AN ANTIBODY

U.S. Pat. No. 4,671,958 issued to Rodwell et al. describes a method for site specific covalent attachment of a compound to an antibody molecule by selectively oxidizing a carbohydrate moiety of the antibody, located outside the antigen binding region of the antibody, to form an aldehyde group and then reacting the resultant aldehyde group with an amine group such as a primary amine, secondary amine, hydrazine, hydrazide, hydroxylamine, phenylhydrazine, or semicarbazide to form an antibody-compound conjugate which is characterized by substantially the same immunospecificity as the unconjugated antibody.

European Patent Application No. 85401695.3 published Mar. 5, 1986 describes methods for preparing and compositions comprising aqueous soluble antibody-metal ion complexes in which a compatible chelator coordinately bound to a metal ion is covalently attached via an amine group of the chelator to an oxidized carbohydrate moiety of an antibody molecule, located outside the antigen binding region of the antibody. The antibody-metal ion complexes are characterized by (1) substantially the same immunospecificity as the unconjugated antibody molecule; and (2) aqueous solubility such that they are suitable for in vivo administration.

European Patent Application No. 85401776.1 published Mar. 26, 1986 describes methods for preparing and compositions comprising aqueous soluble antibody-therapeutic agent conjugates in which a therapeutic agent is attached, either directly or through a linker, via an amine group to an oxidized carbohydrate moiety of an antibody molecule, located outside the antigen binding region of the antibody. The antibody-therapeutic agent conjugates are characterized by (1) substantially the same immunospecificity as the unconjugated antibody molecule; and (2) aqueous solubility such that they are suitable for in vivo administration.

U.S. Pat. Nos. 4,419,444 and 4,217,338 issued to Quash describe a method for attaching an amino-containing solid, insoluble support, such as latex spheres, agarose or dextran beads or activated glass beads, to an oxidized carbohydrate residue of an organic compound such as a glycolipid, glycoprotein or a polysaccharide.

SUMMARY OF THE INVENTION

The present invention provides novel and improved antibody compositions comprising an antibody or antibody fragment having a high mannose-containing carbohydrate moiety located in a portion of the antibody which is not part of nor directly involved with the antigen binding region of the antibody or antibody fragment. As used throughout the present application, the term a "high mannose-containing" antibody molecule is intended to mean an antibody molecule which has at least four mannose residues and no more than nine mannose residues of a $Glc_3Man_9GlcNAc_2$ precursor oligosaccharide per N-linked carbohydrate moiety.

The present invention provides antibody-compound conjugates, antibody-linker intermediates, and antibody-linker compound conjugates prepared using the high mannose-containing antibody compositions. Also provided are methods for preparing and methods for using the novel and improved compositions for a wide variety of in vivo and in vitro applications.

The antibody compositions of the present invention provide the following advantages over conventional antibodies:

(1) upon oxidation yield a significantly increased number of sites outside the antigen binding region for site specific coupling of a compound;

(2) a significantly increased specific activity of antibody conjugates prepared by attaching a compound to a carbohydrate moiety of the antibody;

(3) additional stability and enzyme resistance of the antibody molecule; and (4) a predictable molecular configuration of the carbohydrate moiety of the antibody.

Additionally, the enzyme inhibitors utilized to prepare the improved antibody compositions are virtually non-toxic. The non-toxicity of the inhibitors utilized is particularly advantageous since there are no deleterions effects on the growth of the antibody-producing cells. Moreover, because the inhibitors are virtually non-toxic when administered to animals or humans, there is no need for labor intensive or time consuming methods to separate the inhibitors from the products obtained from the cell supernatants.

The present invention may be more fully understood by reference to the following detailed description of the invention and non-limiting illustrative examples of specific embodiments of the invention.

DETAILED DESCRIPTION OF THE INVENTION

The present invention is directed to novel and improved antibody compositions in which a carbohydrate moiety is modified to yield an increased number of coupling sites for the site specific attachment of a compound to an area of the antibody which is not part of nor directly involved with the antigen binding site of the antibody. Thus, the method of the invention provides antibodies having an increased number of sites for coupling compounds to prepare improved antibody-compound conjugates in which the essential characteristics of the antibody or antibody fragment, such as immunospecificity and immunoreactivity, are not significantly changed.

As used throughout this application, the terms "antibody" and "antibody molecule" are intended to encompass whole antibodies as well as antibody fragments, including, but not limited to half antibody molecules (a single heavy: light chain pair), Fab, Fab' and (Fab')$_2$ fragments, which contain carbohydrate moieties that can be modified using the reaction scheme described herein.

Monoclonal antibodies directed against any determinant of any antigen or any hapten can be used in the present invention. Such determinants include, but are not limited to determinants of: tumor, bacterial, fungal, viral, parasitic, mycoplasmal, histocompatability, differentiation and other cell membrane antigens, pathogen surface antigens, toxins, enzymes, allergens, drugs, any biologically active molecules, etc. In some instances, a combination of monoclonal antibodies reactive with different antigenic determinants can be used.

The compound attached to the novel and improved antibody compositions of the present invention is selected according to the purpose of the intended application (e.g., killing, prevention of cell proliferation, hormone therapy, target imaging, or gene therapy, cell sorting, or separation schemes etc.). Such compounds may include, for example, pharmaceutical agents, toxins, fragments of toxins, alkylating agents, enzymes, antibiotics including such as antibacterials, antifungals, antimycoplasmals, antivirals, etc., antimetabolites, antiproliferative agents, antineoplastic agents including such as inorganic platinum-containing compounds, e.g., cis-diammine-dichloroplatinum-(II) (cisplatin), etc., hormones, neurotransmitters, DNA, radioopaque dyes, radioactive isotopes including non-metallic radioactive isotopes such as I-123, I-131, etc. and radioactive metal ions, fluorogenic compounds, marker compounds, lectins, compounds which alter cell membrane permeability, and insoluble matrices, such as dextrans, agaroses, polystyrenes, polyvinyls, polyvinylalchols, polyacrylamides, and derivatives thereof, glasses, latices and other suitable polymers. Table I of European Patent Application No. 85401776.1 lists some therapeutic agents that can be used in the present invention and is incorporated herein by reference. In no way is Table I, however, meant to be an exhaustive list. Finally, a combination of compounds can be site specifically coupled to a modified antibody composition to form the improved antibody conjugates of the invention.

METHOD OF PREPARATION

According to the method of the invention, cells which produce monoclonal antibodies are treated in vitro in culture medium with an effective amount of a glycosidase inhibitor, including, but not limited to: castanospermine, norjirimycin, 1-deoxynojirimycin, N-methyl-1-deoxynojirimycin, bromocenduritol, 1-deoxymannojirimycin, swainisonine, etc. The high mannose-containing antibody compositions are obtained from the supernatant of the treated in vitro cell cultures using techniques of protein purification known to those of skill in the art.

According to the present invention, cells which produce monoclonal antibodies are incubated in vitro in any suitable culture medium containing a glycosidase inhibitor at a concentration of at least about 20-400 $\mu$g/ml. Because the glycosidase inhibitors are virtually non-toxic and do not interfere significantly with the growth of the cells in culture or secretion of the modified glycoproteins, the upper limit on the concentration of glycosidase inhibitor is not critical and can be determined without undue experimentation by one of ordinary skill.

In practice, monoclonal antibody-producing cells are incubated in culture medium such as Dulbecco's modification of Eagle's Minimal Essential Medium (DMEM) supplemented with about 1% glutamine and 10-20% fetal calf, horse or AGG horse serum containing at least about 20-400 $\mu$g/ml of a glycosidase inhibitor such as castanospermine, norjirimycin, 1-deoxynojirimycin, N-methyl-1-deoxynojirimycin, bromocenduritol, 1-deoxymannojirimycin, swainisonine, etc. The culture medium is maintained at about 37° C. at a pH of about 7.2. The high mannose-containing antibodies are obtained from the supernatant of the treated-cell cultures using any technique of protein purification, such as gradient elution using a protein-A Sepharose column, etc; known to those of ordinary skill.

The antibody molecules produced according to the present invention comprise modified antibody compositions having at least 4 mannose residues per N-linked carbohydrate moiety of the antibody molecule. The "high mannose-containing" antibody molecules of the invention contain 4, 5, 6, 7, 8 or 9 of the mannose residues which are part of the original Glu$_3$Man$_9$NAcGlc$_2$ oligosaccharide precursor per N-linked carbohydrate moiety attached to the protein moiety of the antibody. The high mannose-containing antibody compositions thus have an increased number of sites available for the site specific attachment of a compound in a part of the antibody which is not part of-nor directly involved with the antigen binding region of the antibody. The antibody compound conjugates of the invention provide conjugates with high specific activity which are characterized by substantially the same immunospecificity as the unconjugated, unmodified antibody.

Cells which produce monoclonal antibodies can be obtained using any of a variety of methods known to those skilled in the art. For example, cell lines obtained using the hybridoma methods originally developed by Kohler and Milstein (reviewed by them in 1980, Sci. Amer. 243:66–74), the human B-cell hybridoma methods described by Kozbor et al., 1983, Immunol. Today 4:72, the EBV-hybridoma methods for producing human monoclonal antibodies described by Cole et al., in Monoclonal Antibodies and Cancer Therapy, Alan R. Liss, Inc., pp. 77–96 (1985) the trioma methods described in U.S. Pat. No. 4,634,666 issued to Engleman et al. and the like are used according to the present invention. Additionally, the quadroma or trioma cell lines described by U.S. Pat. No. 4,474,893 issued to Reading can also be used according to the present invention. These latter trioma and quadroma cell lines produce "recombinant monoclonal antibodies" having affinity for more than one desired antigenic target.

ATTACHMENT OF COMPOUNDS

The high-mannose-containing antibody compositions of the invention are advantageously used to prepare antibody-compound conjugates having an increased number of compound molecules. As detailed below, the carbohydrate side chains of a high mannose-containing antibody or antibody fragment can be selectively oxidized to generate aldehydes. Alternatively, the carbohydrate side chains of a high mannose-containing antibody or antibody fragment may be selectively modified by an enzyme making them more suitable for subsequent oxidation by chemical or enzymic means.

The resulting aldehydes are then reacted with an amine group, (e.g., ammonia derivatives such as primary amine, secondary amine, hydroxylamine, hydrazine, hydrazide, phenylhydrazine, alkoxyamine, phenyoxyamine, semicarbazide or thiosemicarbazide) of a compound, a linker or a linker-compound intermediate (see Section 4.2.4., infra) to form a Schiff's base or reduced Schiff's base (e.g., imine, enamine, oxime, hydrazone, phenylhydrazone, semicarbazone, thiosemicarbazone or reduced forms thereof).

METHODS OF CHEMICAL OXIDATION

Oxidation of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, In organic Reactions 2, p.341; Bunton, 1965, Oxidation in Organic Chemistry, Vol. 1 (Wibert, ed.), Academic Press, New York, p.367.

Oxidation of the high mannose-containing antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 20 mM and preferably 1.0 to 10 mM. The amount of the oxygen acid or salt thereof depends on the kind of antibody, but generally it is used in excess, for example, two to ten times as much as the amount of the oxidizable carbohydrate. The optimal amount, however, can be determined by routine experimentation.

In the process for oxidizing antibodies with oxygen acids or salts thereof, the optional ranges include a pH of from about 4 to 8, a temperature of from 0° to 37° C., and a reaction period of from about 15 minutes to 12 hours.

During the oxidation of the high mannose-containing antibody with an oxygen acid or a salt thereof, light is preferably excluded to prevent over oxidation of the glycoprotein.

PREPARATION OF ANTIBODY-CONJUGATES

The antibody conjugates (or antibody linker-intermediates) of the invention are produced by reacting an oxidized carbohydrate moiety of a high mannose-containing antibody with a compound, a linker or a linker-compound intermediate having an available amine group selected from the group consisting of primary amine, secondary amine, hydrazine, hydrazide, hydroxylamine, phenylhydrazine, alkoxyamine, phenoxyamine, semicarbazide, and thiosemicarbazide groups. The immediately resulting products contain a carbon-nitrogen double bond resulting from elimination of a molecule of water from the initial addition products:

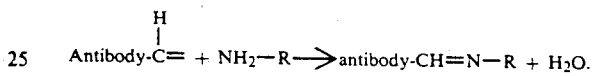

For a general discussion of the reaction of aldehydes with amine-containing compounds, see March, 1978, In Advanced Organic Chemistry: Reactions Mechanisms and Structure, McGraw Hill Co., New York, pp.824–825.

A solution of the oxidized antibody at a concentration of from about 0.5 to 20 mg/ml is mixed with a compound or linker (molar ratios of reactive amine group to antibody aldehyde ranging from about 1 to about 10,000) and the solution incubated for from about 1 to 10 hours. Suitable temperatures are from 0° to 37° C. and pH may be from about 6 to 8.

STABILIZATION OF THE ANTIBODY CONJUGATES

After the antibody-conjugates (or antibody-linker intermediates) have been formed between the antibody and a compound, linker or linker-intermediate, they can optionally be stabilized with a suitable reducing agent, such as sodium cyanoborohydride or sodium borohydride. Reducing agent is generally added to a molar excess of from about 10 to 100 fold molar excess over available aldehyde groups. For a general discussion, see Jentoft and Dearborn, 1979, J. Biol. Chem. 254:4359.

DIRECT ATTACHMENT OR ATTACHMENT VIA A LINKER

According to the invention, a high mannose-containing antibody composition can be covalently attached to a compound directly through an amine group of the compound, thus forming an improved antibody-compound conjugate. Suitable reactive amine groups include those selected from the group consisting of primary amine, secondary amine, hydrazine, hydrazide, hydroxylamine, phenylhydrazine, alkoxyamine, phenoxyamine, semicarbazide and thiosemicarbazide groups.

Alternatively, a high mannose-containing antibody composition can be covalently attached to a compound through an intermediate linker having at least two reactive groups, one an amine group to react with the improved antibody and one to react with the compound.

The linker, which includes any compatible compound, must be chosen such that the reaction with antibody (or compound) does not adversely affect antibody reactivity and selectivity. Moreover, if the compound attached is a therapeutic agent, such attachment must not destroy the activity of the therapeutic agent. Suitable linkers for reaction with oxidized carboydrate moieties of antibodies or antibody fragments include those containing an amine selected from the group consisting of primary amine, secondary amine, hydrazine, hydrazide, hydroxylamine, phenylhydrazine, alkoxyamine, phenoxyamine, semicarbazide, and thiosemicarbazide groups. Such reactive functional groups may exist as part of the structure of the linker, or may be introduced by suitable chemical modification of linkers not containing such groups.

The compound can be attached to the linker before or after the linker is attached to the antibody molecule. In certain applications, it may be desirable to first produce an antibody-linker intermediate in which the linker is free of an associated compound. Depending upon the particular application, a specific compound can then be covalently or coordinately attached to the linker. In other applications, it may be desirable to first produce a linker compound intermediate by either covalently or coordinately attaching a compound to the linker moiety. The linker-compound intermediate is then covalently attached via a reactive amine group to an oxidized carbohydrate moiety of an improved antibody.

Of additional interest are "branched linkers" which have multiple sites for attachment of compounds. For multiple site linkers, a single covalent attachment to an antibody or antibody fragment would result in an antibody-linker intermediate capable of binding a compound at a number of sites.

In another embodiment, cleavable linkers can be used which are susceptible to cleavage by a variety of mechanisms. Peptide linkers which are susceptible to cleavage by enzymes of the complement system, urokinase, tissue plasminogen activator, trypsin, plasmin, or another enzyme having proteolytic activity may be used. In one method of the present invention, a compound is attached via a linker susceptible to cleavage by complement. The antibody is selected from a class which can activate complement. The antibody-linker-compound conjugate, thus, activates the complement cascade and releases the compound at the target site. According to another method of the present invention, a compound is attached via a linker susceptible to cleavage by enzymes having a proteolytic activity such as urokinase, a tissue plasminogen activator, plasmin, or trypsin or the like.

In still another embodiment, it may be necessary to construct the linker in such a way as to optimize the spacing between the compound and the antibody. This may be accomplished by use of an organic linker of the general structure

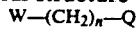

wherein W is either —NH—CH$_2$— or —CH$_2$—;
Q is an amino acid, peptide; and
n is an integer from 0 to 20.

In still other embodiments, the linker may comprise a spacer element and a cleavable element. The spacer element serves to position the cleavable element away from the core of the antibody molecule such that the cleavable element is more accessible to the enzyme responsible for cleavage. Certain of the "branched linkers" described above may serve as spacer elements.

When the compound to be attached is a metal ion, the linker is utilized to attach such compound to an improved antibody molecule is a compatible chelator. The term "a compatible chelator" is intended to mean any compound that (1) is able to donate electrons and combine by coordinate bonding with a metal ion to form structures called chelates or chelation complexes and (2) is suitable for covalent attachment to an antibody or antibody fragment without loss of the ability to chelate metal ions and without destruction of the immunospecificity of the antibody molecule. Compatible chelators include but are not limited to derivatives of diethylenetraiminepentaacetic acid (DTPA), ethylenediaminetetraacetic acid (EDTA), dimercaptosuccinic acid, 2,3-dimercaptopropanesulfonic acid, metallothioein and cryptates, such as those described by Gansow et al., (1981, J. Heterocyclic Chem. 18:297).

According to the present invention, suitable compatible chelators for reaction with an oxidized carbohydrate moiety of a modified antibody or antibody fragment include those containing an amine selected from the group consisting of primary amine, secondary amine, hydroxylamine, hydrazine, hydrazide, phenylhydrazine, alkoxyamine, phenoxyamine, semicarbazide and thiosemicarbazide groups. Such reactive functional groups may exist as part of the structure of the chelator, or may be introduced by suitable chemistry onto chelators not containing such groups.

For example, DTPA lacks an appropriate amine group for facile attachment to oxidized carbohydrate. However, chemical modification can produce a variety of suitable derivatives, such as amine-containing derivatives of mixed anhydrides of DTPA including, but not limited to p-aminoaniline-DTPA, hydrazide-DTPA, phenylhydrazide-DTPA, hydroxylamine-DTPA, semicarbazide-DTPA, thiosemicarbazide-DTPA, polyethyleneimine-DTPA, p-phenylenediamine-DTPA, DTPA mono[(4-aminophenyl)methyl amide and amino acid-containing derivatives of DTPA, including, but not limited to α-N-DTPA-L-lysine, glycyl-tyrosyl-lysine-DTPA and L-lysine benzyl ester-DTPA.

APPLICATIONS

The improved antibody-compound conjugates of the invention, including antibody-therapeutic agent conjugates and antibody-metal ion complexes, are advantageously used in a variety of in vivo and in vitro applications.

IN VIVO APPLICATIONS

When utilized for in vivo applications, the antibody-compound conjugates possess aqueous solubility such that they are suitable for in vivo administration via any parenteral route. The intravenous route of administration is generally preferred.

The antibody-compound conjugates are administered in any suitable adjuvant, including serum or physiological saline, with or without another protein, such as human serum albumin. Dosages of the conjugates is readily determined by one of ordinary skill and may differ depending upon the nature of the in vivo application and the compound used.

Attachment of a compound which is a non-metallic radioactive isotope to an improved antibody composition according to the invention results in compositions having high specific radioactivity which are advantageously useful for diagnostics or imaging applications and for therapeutic purposes. For example, attachment of a non-radioactive isotope such as I-123 forms an antibody conjugate which is useful for in vivo diagnostic applications. Attachment of an isotope such as I-131 forms an antibody conjugate which is useful for in vivo therapeutic applications.

When the compound attached to an improved antibody composition is a therapeutic agent, the antibody-therapeutic agent conjugates are useful for treatment of a variety of cellular disorders including neoplasms such as adenomas, cancers, and hyperplasias; certain immunological disorders, including graft-versus-host diseases (e.g., after bone marrow transplantation); immune suppressive disorders, (e.g., after kidney or bone marrow transplantation); cardiovascular diseases such as those associated with the formation of atherlosceclortic plaques, etc,; infections induced by viral, bacterial, fungal, mycoplasmal, or parasitic agents, etc.

When the compound attached to an improved antibody composition is a metal ion, the linker used is a compatible chelator and the conjugate formed is termed an antibody-metal ion complex. Depending upon the particular metal ion attached, the complexes are used for therapeutic or diagnostic purposes. For example, attachment of beta or alpha emitting metal ions such as Scandium-46, Scandium-47, Scandium-48, Gallium-72, Gallium-73, Yttrium-90, Bismuth-211, Bismuth-212, Bismuth-213, Bismuth-214, or Lead-212 forms complexes which are suitable for therapeutic uses for targeted cell killing. Additionally, attachment of metal ions such as Indium-111, Technetium-99m and Copper-67, Rhenium-186, Rhenium-188, forms complexes which are are useful for diagnosis and imaging target sites in vivo. Alternatively, complexes of radioactive metal ions such as positron emitting ions including Scandium-43, Scandium-44, Iron-52, Cobalt-55 and Gallium-68 are used for imaging with positron emission tomography. Finally, complexes of non-radioactive paramagnetic metal ions such as Iron-54, Iron-radioactive 56, Iron-57, Iron-58, Gadolinium-157 and Manganese-55 are used for imaging by nuclear magnetic resonance spectroscopy.

When used for in vivo therapeutic applications, the method of the invention comprises: treatment of a cellular disorder by administering to an animal or a human an effective amount of an aqueous soluble improved antibody-therapeutic agent conjugate of the invention which is immunoreactive with and immunospecific for a target site associated with the cellular disorder and substantially non-immunoreactive with and non-immunospecific for tissue not associated with the cellular disorder.

When used for in vivo diagnostic imaging applications, the method of the invention comprises imaging a specific tissue by:

(a) administering to an animal or a human an effective amount of an improved antibody compound conjugate which is immunoreactive with and immunospecific for an antigenic determinant of the specific tissue and non-immunospecific for non-specific tissue and in which the antigenic determinant is not found in substantial amounts in non-specific tissue; and (b) detecting whether the antibody compound conjugate localized at the specific tissue.

IN VITRO APPLICATIONS

The improved antibody-compound conjugates of the invention are useful for a variety of in vitro applications including separations and affinity purifications, immunoassays, cell sorting, electrophoretic analysis, histology, cytology, etc. All these applications depend upon the ability of the antibody or antibody fragment to specifically distinguish chemical compounds of slightly different structure and upon the ability of the attached compound to provide a detectable signal or a means for modulating a detectable signal. Since the improved antibody compositions provide an increased number of coupling sites for the compounds, they afford an enhanced sensitivity for all the in vitro applications. The compounds used to prepare improved antibody-compound conjugates for in vitro applications can be aqueous soluble compounds.

For example, when used for an in vitro method for testing for a particular antigen, the method of the invention comprises: (a) mixing an improved antibody-compound conjugate of the invention with a sample suspected of containing the particular antigen, the antibody compound conjugate being immunoreactive with and immunospecific for the antigen, and (b) detecting whether or not an interaction of the antibody compound conjugate and any antigen in the sample occurs.

The following Examples are presented for purposes of illustration and not by way of limitation on the scope of the invention.

CARBOHYDRATE MOIETIES OF ANTIBODY OBTAINED FROM CELLS TREATED WITH A GLYCOSIDASE INHIBITOR

The following experiments demonstrate that monoclonal antibodies obtained from cells treated with a glycosidase inhibitor according to the present invention have significantly different carbohydrate patterns from those observed in analogous antibody from untreated control cells.

The glycosidase inhibitor employed in the following series of experiments was deoxymannorjirmycin (DMN).

The antibody employed in this series of experiments was a monoclonal antibody (IgG1) reactive with human breast and colon cancer obtained from hybridoma cell line ATCC No. B72.3 (hereinafter "B72.3 antibody") described in U.S. Pat. No. 4,522,918 issued to Schlom et al. (See, Nuti et al., 1982, Int. J. Cancer 29:539–45).

Experimental cultures of the B72.3 hybridoma cell line were incubated for 3–4 days at 37° C. in Dulbecco's modification of Eagle's Minimal Essential Medium (DMEM) tissue culture medium supplemented with 10% fetal calf serum and 1% glutamine and containing deoxymannojirimycin (DMN) at a concentration of 0.2 mg/ml. Control cultures of B72.3 cells were similarly incubated without DMN.

The carbohydrate moieties of the whole B72.3 antibody molecules obtained from both DMN-treated and control cultures were analyzed using three separate hydrolyses as follows:

(1) amino sugars such as glucosamine and galactosamine were analyzed after hydrolysis in 6 N HCl at 100° C. for 3 hours;

(2) neutral sugars such as galactose, mannose and fucose were analyzed after hydrolyis in 4 M trifluoroacetic acid (TFA) at 100° C. for 2 hours; and (3) sialic acid was analyzed after hydrolysis in 20 mM $H_2SO_4$ at 80° C. for 1 hour. The neutral sugars were converted to amino-containing forms prior to analysis. The hydrolyzed samples were analyzed by cation-exchange HPLC, using an orthophthaldehyde reactor and fluorescence detector. Results are tabulated in Table 1.

TABLE 1

B7.23 MONOCLONAL ANTIBODIES FROM DMN-TREATED HYBRIDOMAS CARBOHYDRATE (CHO) CONTENT

| CHO Residue | AMOUNT CHO (n moles) | | |
|---|---|---|---|
| | Untreated | Control Untreated[a] | DMN treated |
| Glucosamine | 9.01 | 8.88 | 3.62 |
| Galactosamine | 1.80 | 1.85 | trace |
| Galactose | 3.24 | 2.96 | —[b] |
| Mannose | 5.58 | 5.25 | 10.43 |
| Fucose | 1.08 | 1.33 | —[b] |
| Sialic acid | 3.96 | 3.48 | trace |

[a] Antibody produced in a large scale production run.
[b] The "—" indicates that the CHO residue was below the level of detection.

As shown in Table 1, B72.3 antibody obtained from cells treated with DMN contained significantly higher number of mannose residues when compared to antibody obtained from untreated, normal cells.

The carbohydrate moieties of B72.3 antibody obtained from DMN-treated cells were digested with endoglycosidase H obtained from Boeringer-Mannhein (Indianapolis, Ind.). The digested antibody was then analyzed using polyacrylamide gel electrophoresis (PAGE). Gels contained 10% acrylamide gel and 4% acrylamide starch (Bio-Rad Molecular Weight Standards, Richmond, Calif.). The gels were electrophoresed at 20 m Amps in Tris-glycine buffer for about one hour. The migration patterns obtained confirmed the presence of a high mannose-containing oligosaccharide side chain on the B72.3 antibody obtained from DMN-treated B72.3 cells which was not present on antibody obtained from untreated control cells.

ENHANCED SPECIFIC ACTIVITY OF ANTIBODY-METAL ION COMPLEXES

The following example demonstrates that an antibody-metal ion complex prepared according to the method of the invention has significantly higher specific activity than the analogous complex prepared using antibody obtained from untreated cells.

Experimental cultures of the B72.3 hybridoma cell line were incubated for 3-4 days at 37° C. in DMEM tissue culture medium supplemented with 10% fetal calf serum and 1% glutamine and containing DMN at a concentration of 0.2 mg/ml. Control cultures of B72.3 cells were similarly incubated without DMN.

The carbohydrate moieties of monoclonal antibodies, isolated from the supernatants of both experimental and control cell cultures were oxidized according to the method of Rodwell et al., 1986, Proc. Nat'l Acad. Sci. USA 83:2632-36.

Briefly, the carbohydrate moieties of the antibodies were oxidized by incubation in the dark with 10 mM NaIO$_4$ in phosphate buffered saline (0.15 M NaCl/0.01 M sodium phosphate; PBS) at pH 6.0 in ice for 1 hour. The antibodies were then purified using a Sephadex ® G-25 column equilibrated with PBS at pH 6.0.

The antibodies having oxidized carbohydrate moieties were then incubated with a derivative of the chelator diethylentriaminepentaacetic acid (DTPA), i.e., glycyltyrosyllysyl diethylentriaminepentaacetic acid (GYK-DTPA) at a two-thousand molar excess of GYK-DTPA at pH 6.0. Sodium cyanoborohydride (Aldrich Chemical Co. Inc., Milwaukee, Wis.) was added to a final concentration of 10 mM. The reaction mixture was incubated overnight in the dark and the samples were concentrated to 2.0 ml. The samples were eluted through a Superose 12 column (Pharmacia Fine Chemicals, Piscataway, N.J.).

Fifty mg of the experimental and control antibody-DTPA intermediate were radiolabeled by incubation with $^{111}$InCl$_3$ (New England Nuclear, Boston, Mass.) in an equal volume of 0.5 M sodium acetate buffer at pH 6.0 for 1 hour. The antibody-chelator metal ion complexes formed (i.e., antibody-GYK-DTPA-$^{111}$In) were separated from free $^{111}$In by elution through a TSK-G3000SW gel column.

The specific radioactivity of the experimental and control antibody-chelator-metal ion complexes is illustrated in Table 2.

TABLE 2

ANTIBODY COMPOUND CONJUGATES: INCREASED SPECIFIED ACTIVITY

| | Specific Activity of B72.3 Antibody-μCi/ μg-GYK-DTPA-$^{111}$ In Complexes | |
|---|---|---|
| Experiment No. | DMN-Treated B72.3 Cells | Untreated Control B72.3 Cells |
| 1 | 10.5 | 3.1 |
| 2 | 11.4 | 3.1 |

As demonstrated in Table 2, antibody-chelator-metal ion complexes having a radiolabeled -metal ion site specifically attached to an antibody obtained from cells treated with DMN have significantly greater specific radioactivity than complexes having antibody obtained from control, untreated cells. Thus, treatment of cells with an agent, such as DMN, which suppresses carbohydrate trimming glycosidases yields monoclonal antibodies with enhanced ability to bind radiolabeled bioactive molecules and provide higher specific activity for target systems.

BIODISTRIBUTION OF ANTIBODY-METAL ION COMPLEXES

This experiment demonstrates that an antibody-metal ion complex according to the present invention is advantageously used for in vivo imaging or detection of tumor xenografts in experimental animals.

The in vivo localization of the antibody-metal ion complexes was evaluated in female nude (nu/nu) mice (Taconic Farms, Germantown, N.Y.) injected subcutaneously with $1 \times 10^6$ LS174T human colon adenocarcinoma cells (Tom et al., 1976, In Vitro 12: 180-91). When the tumors were 20 about 100-400 mg, antibody-metal ion complexes were injected intravenously into 3-6 LS174T tumor-bearing and non-tumor bearing (control) mice.

Experimental and control radiolabeled antibody-metal ion complexes were prepared as described above using antibody obtained from DMN-treated and untreated, control B72.3 cells. An aliquot of 10 ml of either experimental or control antibody complex was injected into 3-6 mice. Animals injected with the radiolabeled complexes were imaged background subtraction at 1 and post-injection using a General Electric Maxi Camera 37 equipped with a parallel hole collimater and an ADAC computer system. Alternatively, animals were sacrificed and dissected at 5 days post-injection to obtain quantitative biodistribution data.

Good localization to the tumor xenografts was observed using both experimental and control $^{111}$In-radiolabeled antibody-metal ion complexes (data not shown).

Table 3 illustrates the biodistribution of antibody-metal ion complexes following intravenous administration of the complexes.

TABLE 3

BIODISTRIBUTION OF ANTIBODY-GYK-DTPA-[111] IN COMPLEXES

| | Tumor-Bearing Animals | | Non-Tumor Bearing Animals | |
|---|---|---|---|---|
| | Ab-DMN-Treated B72.3 Cells | Ab-Control B72.3 Cells | Ab-DMN-Treated B72.3 Cells | Ab-Control B72.3 Cells |
| | Organ/Blood Ratio | | | |
| Liver | 2.65[a] | 2.45[a] | 0.60[b] | 0.66[b] |
| Spleen | 1.64 | 1.57 | 0.53 | 0.66 |
| Tumor | 11.43 | 11.57 | — | — |
| | % Injected Dose/Organ | | | |
| Liver | 5.1 | 5.6 | 9.9 | 10.9 |
| Spleen | 3.3 | 3.5 | 8.9 | 11.1 |
| Tumor | 26.6 | 25.5 | — | — |

[a]Total CPM × 10$^{-6}$ in liver of tumor-bearing animals:
0.6 Ab-DMN treated B72.3 Cells
0.4 Ab-Control B72.3 Cells.
[b]Total CPM × 10$^{-6}$ in liver of non-tumor bearing animals:
1.6 Ab-DMN Treated B72.3 Cells
1.2 Ab-Control B72.3 Cells As shown in Table 3, both total percent antibody-complex delivered to the tumor and the organ/blood ratio of the tumor using antibody site specifically radiolabeled according to the present invention represent a significant target specific delivery. Additionally, the total percent antibody complex recovered from the spleen and liver of control non-tumor animals was significantly higher than that from tumor-bearing animals, suggesting that at least a portion of the accumulation seen in tumor-bearing animals represents an active diversion of antibody from these non-target liver and spleen sites to target areas of tumor proliferation.

Finally, the results presented in Tables 2 and 3 clearly demonstrate that antibody-complexes prepared using antibody obtained from DMN-treated cells have very high specific activity and are selectively delivered to target antigen sites when administered in vivo to tumor-bearing animals and are not delivered to normal non-target sites, such as the liver and spleen, when administered to non-tumor bearing animals.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method for treating a cellular disorder, comprising: administering to an animal or a human a therapeutically effective amount of an aqueous soluble antibody-compound conjugate which comprises a compound attached via a covalent bond to an oxidized carbohydrate moiety of a high-mannose containing antibody or antibody fragment, in which the oxidized carbohydrate moiety is not part of nor directly involved with the antigen binding site of the antibody or antibody fragment, to form an antibody-compound conjugate being characterized by substantially the same immunospecificity as the unconjugated antibody or antibody fragment and which is immunoreactive with and immunospecific for a target site associated with the cellular disorder and substantially non-immunoreactive with and non-immunospecific for tissue not associated with the cellular disorder.

2. A method for treating a cellular disorder, comprising: administering to an animal or a human a therapeutically effective amount of an aqueous soluble antibody-linker compound conjugate which comprises a compound attached either covalently or coordinately to a linker which is attached via a covalent bond to an oxidized carbohydrate moeity of a high mannose-containing antibody or antibody fragment, in which the oxidized carbohydrate moiety is not part of nor directly involved with the antigen binding site of the antibody or antibody fragment, to form an antibody-linker compound conjugate being characterized by substantially the same immunospecificity as the unconjugated antibody or antibody fragment and which is immunoreactive with and immunospecific for a target site associated with the cellular disorder and substantially non-immunoreactive with and non-immunospecific for tissue not associated with the cellular disorder.

3. A method for in vivo imaging a specific tissue comprising:
    (a) administering to an animal or a human an effective amount of an antibody-compound conjugate which comprises a compound attached via a covalent bond to an oxidized carbohydrate moiety of a high-mannose containing antibody or antibody fragment, in which the oxidized carbohydrate moiety is not part of nor directly involved with the antigen binding site of the antibody or antibody fragment, to form an antibody-compound conjugate being characterized by substantially the same immunospecificity as the unconjugated antibody or antibody fragment which is immunoreactive with and immunospecific for an antigenic determinant of the specific tissue and is not found in substantial amount in non-specific tissue; and
    (b) detecting whether the antibody compound conjugate localized at the specific tissue.

4. A method for in vivo imaging a specific tissue comprising:
    (a) administering to an animal or a human an effective amount of an antibody-linker compound conjugate which comprises a compound attached either covalently or coordinately to a linker which is attached via a covalent bond to an oxidized carbohydrate moeity of a high mannose-containing antibody or antibody fragment, in which the oxidized carbohydrate moiety is not part of nor directly involved with the antigen binding site of the antibody or antibody fragment, to form an antibody-linker compound conjugate being characterized by substantially the same immunospecificity as the unconjugated antibody or antibody fragment which is immunoreactive with and immunospecific for an antigenic determinant of the specific tissue and is not found in substantial amount in non-specific tissue; and
    (b) detecting whether the antibody-linker compound conjugate localized at the specific tissue.

5. The method of claim 1, in which the compound is an amine containing derivative of an anthracycline antibiotic.

6. The method of claim 1, in which the compound is an amine containing derivative of cisplatin.

7. The method of claim 1, in which the compound is an amine containing derivative of a compound selected from the group consisting of fluorouracil, bleomycin, methotrexate, aminopterin, adriamycin, velban and alkeran.

8. The method of claim 1, in which the compound is an antibacterial, antiviral, antifungal, antiparasitic or antimycoplasmal agent.

9. The method of claim 1, in which the compound is selected from the group consisting of a radioactive isotope, a non-metallic radioactive isotope and a radioactive metal ion.

10. The method of claim 2, in which the compound is an amine containing derivative of an anthracycline antibiotic.

11. The method of claim 2, in which the compound is an amine containing derivative of cisplatin.

12. The method of claim 2, in which the compound is an amine containing derivative of a compound selected from the group consisting of fluoruracil, bleomycin, methotrexate, aminopterin, adriamycin, velban and alkeran.

13. The method of claim 2, in which the compound is an antibacterial, antiviral, antifungal, antiparasitic or antimycoplasmal agent.

14. The method of claim 2, in which the compound is selected from the group consisting of a radioactive isotope, a non-metallic radioactive isotope and a radioactive metal ion.

15. The method of claim 3, in which the compound is selected from the group consisting of a radioactive isotope, a non-metallic radioactive isotope and a radioactive metal ion.

16. The method of claim 4, in which the compound is selected from the group consisting of a radioactive isotope, a non-metallic radioactive isotope and a radioactive metal ion.

* * * * *